United States Patent [19]

Schuurs et al.

[11] E Re. 29,169

[45] Reissued Apr. 5, 1977

[54] PROCESS FOR THE DEMONSTRATION AND DETERMINATION OF REACTION COMPONENTS HAVING SPECIFIC BINDING AFFINITY FOR EACH OTHER

[75] Inventors: Antonius Hermanus Wilhelmus Maria Schuurs; Bauke Klaas van Weemen, both of Oss, Netherlands

[73] Assignee: Akzona Incorporated, Asheville, N.C.

[22] Filed: Jan. 26, 1976

[21] Appl. No.: 652,362

Related U.S. Patent Documents

Reissue of:

[64] Patent No.: 3,791,932
Issued: Feb. 12, 1974
Appl. No.: 221,447
Filed: Jan. 27, 1972

[30] Foreign Application Priority Data

Feb. 10, 1971 Netherlands ..... 7101728

[52] U.S. Cl. ..... 195/103.5 A; 424/12; 23/230 B

[51] Int. Cl.[2] ..... G01N 31/14

[58] Field of Search ..... 195/103.5 R, 103.5; 424/12; 23/230 B

[56] References Cited

UNITED STATES PATENTS 3,654,090 4/1972 Schuurs et al. ..... 195/103.5 R

*Primary Examiner*—Alvin E. Tanenholtz
*Attorney, Agent, or Firm*—Francis W. Young; Hugo E. Weisberger

[57] ABSTRACT

The present invention relates to a process for the determination of a component of the reaction between a specific binding protein and the substance being specifically bound by such a protein comprising reacting the component to be determined with its binding partner in an insolubilized form, separating the solid phase of the reaction mixture from the liquid phase, reacting the solid phase with a determined amount of a coupling product of the substance to be determined with an enzyme, and finally determining the enzyme activity of the liquid or solid phase of the reaction mixture obtained.

6 Claims, No Drawings

PROCESS FOR THE DEMONSTRATION AND DETERMINATION OF REACTION COMPONENTS HAVING SPECIFIC BINDING AFFINITY FOR EACH OTHER

Matter enclosed in heavy brackets [ ] appears in the original patent but forms no part of this reissue specification; matter printed in italics indicates the additions made by reissue.

For the demonstration and determination of substances playing a prominent part in biochemical processes, i.e. low molecular substances, such as vitamins and steroids, or high molecular ones, such as proteins and carbohydrates, it is often possible to employ reactions of these substances with proteins having a specific binding affinity for these substances. Thus, it is possible to determine the concentration of a steroid by employing a protein capable of binding this steroid specifically. As examples of such combinations are mentioned cortisol and transcortin, 17β-oestradiol and the oestradiol-binding receptor protein of the uterus.

It is also possible to link a low molecular substance chemically with a protein, and to inject this conjugate into a test animal, which then reacts by forming antibodies against, among others, the low molecular substance. The latter is in this case to be regarded as a so-called hapten. The antibodies against the hapten may be regarded as a special case of specific binding proteins.

High molecular substances, such as simple and conjugated proteins and carbohydrates, are capable of causing the formation of antibodies on being injected into animals in the correct experimental conditions. Between these antibodies and the injected high molecular substance, the antigen, there is again question of specific binding affinity.

Determination methods in which these specific binding affinities are employed, are often based on the competition between the substance to be determined in the sample and the known quantity of the same substance, labelled radioactive, for a limited quantity of its binding partner. The quantity of substance to be determined determines what part of the radioactive labelled substance can be bound by its binding partner. It is also possible to determine an unknown quantity of specific binding protein by reacting a sample of it with a certain quantity of radioactive labelled, specific binding substance. The terms by which these methods are designated in the literature, depend upon the nature of the specific binding protein. They speak of "competitive protein binding assays," where receptor or transport proteins are used, and of "radioimmunological determinations" where antibodies are employed as specific binding protein.

Instead of labelling one of the components of the above-described reactions with a radioactive isotope, it is also possible to employ an enzyme as a labelling substance. Where use is made of the binding affinity between a low molecular substance and its specific binding protein, the low molecular substance can be coupled with an enzyme. The coupling product, low molecular substance/enzyme, can then be used in experimental set-ups as described above. Where use is made of the binding affinity between an antigen and its antibody, the antigen may, for example, be coupled with an enzyme instead of labelling it with a radioactive isotope as is conventional in radioimmunological methods.

For all the methods in which such a labelled reaction component is employed, a suitable method for separating the free labelled compound attached to the binding partner, is essential. Dependent upon the nature of the substances participating in the reaction, various separation methods can be employed, for example electrophoresis, gel filtration, selective adsorption, application of one of the reaction components in an insolubilised form, and application of antibodies against one of the reaction components, also in an insolubilised form.

In spite of the high sensitivity that can be achieved by these methods, it is not always possible to demonstrate or determine substances occurring in extremely low concentrations in, for example, serum or urine. Thus, it is very difficult and often impossible to demonstrate adrenocorticotrophic hormone (ACTH) by a radioimmunological method, unless one has the disposal of a very rare antiserum containing antisubstances with an extremely high binding affinity for ACTH.

Also determinations of smaller peptide hormones such as oxytocin in non-extracted serum, causes great difficulties, because the required sensitivity cannot be reached.

Although, in principle, the immunoligical cross-reaction between HCG and LH enables both hormones to be determined with one test-system, most methods for the determination of human chorionic gonadotrophin (HCG) by a coupling product of HCG and an enzyme cannot be used for the demonstration and determination of luteinizing hormone (LH). This is due to the fact that LH occurs in much lower concentrations in blood and urine than HCG during pregnancy, so that the sensitivity of the test systems are insufficient. This shortage of sensitivity can be decreased by extracting the substance to be determined from the medium in which it occurs or by concentrating the medium. These methods, however, are very laborious, and the results often unsatisfactory.

A process has now been found for the demonstration and determination of a component of the reaction between specific binding proteins and the substances that can be specifically bound by these proteins, using the known binding affinity of such components for each other, which comprises reacting the component to be determined with its binding partner, which has been or is insolubilised, separating the solid phase of the reaction mixture from the liquid phase, reacting the solid phase with a coupling product obtained by binding a substance capable of reacting specifically with one of the reaction componets, to an enzyme, and finally determining the enzyme activity of the liquid or the solid phase in the reaction mixture obtained, which is a measure for the quantity of the substance to be determined.

The binding partner required for the determination of the component present in an unknown quantity, is employed in an insoluble form. The determination can take place by adding the binding partner to the reaction mixture in an insoluble form and reacting the mixture in a heterogeneous medium, but the binding partner can also be added in a dissolved form, after which it can be insolubilised by adding antisubstances against it.

The substance capable of reacting specifically with one of the reaction components, and which is employed coupled with an enzyme, may be the other reaction component, but also a third substance that must possess a specific affinity for one of the components of the reaction.

The method can be applied to the various reaction systems described above, i.e. antigen/antibody, hapten-/antibody and a low molecular substance/specific binding protein. As third substance a second antibody may occur, that is to say, an antibody against the gamma-globulin fraction of the species of animal in which the first antibodies have been generated. This situation may occur in the systems antigen/(first) antibody and hapten/(first) antibody. As third substance may also occur an antibody against a specific binding protein.

The essence of the method is the performance in two steps, in between which a separation takes place of the liquid and the solid phase of the reaction mixture. With the solid phase the second step is performed. Only in this stage the enzyme coupling product is employed and the enzyme activity determined.

The most important advantages of the method found are:

1. The first step can be performed in a larger volume than is desirable or possible for the second step. This is of great importance when the substance to be determined occurs in too low concentrations to be determined by known methods.
2. In the liquid to be examined substances may be present influencing the reactions in the second step unfavourably. Expecially the enzyme present in the coupling product and the enzymatic catalysing reaction may be sensitive to disturbing substances in the test liquid.

The method found can especially be employed for the determination of substances present in body liquids such as hormones, their antibodies and specific binding proteins, as well as enzymes. Also factors of blood-clotting, fibrinolysis and complement systems, pathological proteins in body liquids, as well as antibodies against pathogenic microorganisms and iso-antibodies can be determined in this manner.

The medium in which the first step of the determination takes place often consists for a large part of test liquid, such as urine or serum. If considered necessary, it can be adjusted to the pH requied for the immunochemical reaction, viz. between 5 and 9, by adding a dry buffer salt or a small volume of a concentrated buffer solution. The medium of the second step is also a buffer of a pH required for the immunochemical reaction. For this purpose phosphate buffers, citrate buffers, tris(hydroxy methyl)-aminomethane, and imidazole buffers can be employed. It may be necessary to use for the relative enzyme reaction a buffer of another composition and pH, which depends upon the enzyme employed.

The manufacture of the insolubilised reaction component can take place in various manners, i.a. dependent upon the properties of this reaction component. Thus, antibodies, specific binding proteins and protein-like antigen can be insolubilised by cross-linking, for example, glutaric aldehyde and chloroformic acid ethyl ester, by physical adsorption or chemical coupling with an insoluble carrier, such as cellulose compounds, agarose, cross-linked dextran, polystyrene and the like, or by coupling with antibodies against the relative protein coupled with an insoluble carrier. Low molecular substances can be bound by methods dependent upon the structure of the low molecular substance and the carrier material. Some of the low molecular substances may already possess groups capable of reacting with the reactive parts on the carrier material: in other cases such groups will have to be introduced by organic chemical reactions.

The manufacture of the enzyme coupling products is also performed by methods dependent upon the properties of the molecules incorporated into the coupling product. A covalent bond of proteins to enzymes can be effected by reagents such as carbodiimides, diisocyanates, glutaric aldehyde and bis-diazobenzidine. The coupling of low molecular substances can take place in various manners. Some of these substances may already possess groups that can be cross-linked with reactive groups of the enzyme; in other cases such groups will have to be introduce by organic chemical reactions. It stands to reason that in the manufacture of these coupling products the original binding properties of the substances bound to the enzyme may not change very much; no more may the enzyme activity be decreased considerably.

The choice of the enzyme that is to form a part of the coupling product, is determined by properties such as the specific binding activity (a high conversion rate raises the sensitivity of the test system) and the simplicity of the determination of the enzyme. The determination of an enzyme catalysing a conversion in which coloured reaction components are involved, is simple. Such colorimetric determinations can be automated in a simple manner.

According to the invention it is also possible to employ enzymes catalysing those conversions in which reaction components are involved that can be determined spectrophotometrically or fluorimetrically. These determinations can also be automated.

In the manufacture of the coupling products enzymes such as catalase, peroxidase, β-glucuronidase, β-B-glucosidase, β-D-galactosidase, urease, glucoseoxidase and galactose-oxidase are preferred, especially the group of the oxidoreductases.

The determinations according to the invention are broadly performed as follows: A certain volume of a test liquid, for example 10 ml, containing a very low concentration of the component to be determined, is mixed with a certain quantity of an insolubilised reaction partner of the substance to be determined. The test liquid may be urine, in which the component to be determined occurs in low concentration, or serum, which has been diluted to diminish the influence of disturbing factors. In order to enable the reaction to be performed in the heterogeneous system, the mixture is agitated. The resulting solid phase is separated from the test liquid, for example by centrifugation, and washed, if considered necessary. The first part of the determination can also be performed by incubating the test liquid with a certain quantity of the reaction partner of the substance to be determined in a dissolved form, after which a quantity of insolubilised antibody against that reaction partner is added and the mixture agitated and finally centrifuged. Separation by filtration and decantation is also possible.

The second part of the determination is performed by resuspending the insoluble substance, which forms the solid phase, preferably in a buffer, and to react it with a certain quantity of a coupling product of the substance to be determined with an enzyme, for example, peroxidase. After a certain time the solid phase is separated again, for example by centrifugation, after which the enzyme activity in the liquid phase is determined. This enzyme activity is a measure for the quantity of substance to be determined in the test liquid. The second part of the determination can also be performed by reacting the insoluble substance from the first part of the determination, with a coupling product obtained by binding a third substance capable of reacting specifically with the reaction component to be determined, with an enzyme. This will be the case when an antibody is determined by the insolubilised corresponding antigen in the first part of the determination, and a second antibody, against the first, which is coupled with an enzyme, is used in the second part of the determination.

The enzyme activity of a phase of the reaction mixture is demonstrated or measured by incubating that phase with a substrate and other substances required for the relative enzyme reaction.

Preferably a reaction is employed in which a coloured compound is formed, or removed, whose adsorption can be easily quantitatively determined.

The form in which the reagents can be used are manifold. The component of the reaction system coupled with an enzyme may have been dissolved in a buffer, or freeze-dried. Also a solid carrier can be used, for example a strip of paper impregnated with the enzyme coupling product.

The insoluble component can be processed in the form of particles of various sizes, such as grains, plates and rods, or in the form of a strip of some or other carrier material.

For the performance of the process according to the invention a test-pack is usually employed, chiefly consisting of:

a. a certain quantity of the enzyme coupling product;
b. a corresponding quantity of one of the components of the reaction system in an insoluble form;
c. a substrate for the determination of the quantity of the enzyme employed.

The test-pack can contain the necessary auxiliaries, if required, to make a dilution series of the sample to be tested for a quantitative determination, such as test tubes, pipettes and flasks containing a diluent, For the determination of antigens or haptens, or their antibodies, the test-pack contains at least:

a. a certain quantity of the coupling product of the antigen or hapten, or an antibody against it, and an enzyme;
b. a corresponding quantity of an insolubilised component of the reaction system antigen/antibody, or hapten/antibody, and
c. a substrate for the determination of the enzyme activity.

The invention is further illustrated by the following examples, which are on no account intended to limit the invention.

EXAMPLE I

Determination of human chorionic gonadotrophin (HCG) in serum.

a. Preparation of HCG-HRP. Five mg of HCG and 20 mg of horse-radish peroxidase (HRP) were dissolved in 2 ml of 0.05 M phosphate buffer of pH 6.2. After 40 $\mu$/ltr of 25 percent glutaric aldehyde solution had been added, the mixture was shaken at room temperature for 2 hours. Then the mixture was centrifuged for 5 minutes at 250 g, after which it was fractionated over Sephadex G-200 in 0.05 M phosphate buffer of pH 6.2. The fractions whose highest percentage of enqyme activity was bound by antibodies against HCG, were used in the test system.
b. Preparation of antibodies against HCG. Antibodies against HCG were generated in rabbits as described by Schuurs et al. in Acta Endocr. (Kbh.) 59, 120 (1968).
c. Preparation of the immuno-adsorbent, anti-HCG-cellulose. The $\gamma$-globulin fraction of the anti-HCG-serum described under b) was prepared by precipitation with 18 percent (w/v) solid $Na_2SO_4$. The precipitate was washed and then taken up in so much 0.05 M borate buffer of pH 8.6 that the ultimate protein concentration was 10 mg/ml. M-aminobenzyloxy methyl cellulose (350 mg) prepared by Gurvich's method, described in Biokhimiya 26, 934 (1961), was suspended in 50 ml of distilled water and diazotized by adding 10 ml of 36 percenthydrochloric acid and, dropwise, 10 ml of 10 percent $NaNO_2$-solution. The supension was centrifuged and washed, and the precipitate resuspended in 43 ml of 0.05 M sodium borate of pH 8.6. $\gamma$-globulin solution prepared 7 ml were added to this suspension. The mixture was stirred for 26 hours at 4° C. centrifuged, and finally washed with 1 ltr of 0.02 M phosphate buffer of pH 6.0.
d. Determination of HCG in serum. A dilution series of HCG (8–4–2–1–0.5–0.25–0 I.U./ml) was prepared with a dilution liquid consisting of one part of man's serum and 2 part of 0.05 M phosphate buffer of pH 6.2. Of each of the thus prepared HCG dilutions 0.5 ml was rotated for 2 hours at room temperature with 0.5 ml of the immuno-adsorbent suspension (4 mg/ml), prepared in accordance with c), and then centrifuged. The precipitate was washed twice, each time with 2 ml of 0.05 M phosphate buffer of pH 6.2. The precipitate was mixed with 1.0 ml of HCG-HRP solution in a suitable dilution, as well as in 0.05 M phosphate buffer of pH 6.2, and rotated again at room temperature for 2 hours.

After centrifugation the enzyme activity was determined in the supernatant liquid by adding 0.5 ml of it to 1.5 ml of a substrate solution consisting of 10 $\mu$l of 30% $H_2O_2$ and 20 mg of 5-amino salicylic acid in 150 ml of 0.02 M phosphate buffer of pH 6.0. After 30 minutes the extinction was measured at 460 nm.

In the test system described a HCG concentration of 0.25 I.U./ml caused a measurable increase in the enzyme activity in the supernatant liquid, while a concentration of 1 I.U./ml caused the maximum increase. In this test the centrifugation step proved to be of decisive significance, as omission of this step gave rise to wrong measuring results of the enzyme activity, i.e. owing to turbidity of the serum and the peroxidase-like activity of it.

The HCG content of serum of pregnant women could be determined in this experimental set-up provided that the serum sample was diluted in the ratio of at least 1:3.

EXAMPLE II

Determination of HCG in low concentrations by means of an enzyme/antigen coupling product.

a. Preparation of antisubstances against rabbit-$\gamma$-globulin. Rabbit-$\gamma$-globulin was isolated from normal rabbit serum by precipitating it with 18 percent (w/v) solid $Na_2SO_4$. Antibodies against it were generated in a sheep. The injection scheme was:

| Day | Quantity | Freund's adjuvant | Manner of injection |
|---|---|---|---|
| 0 | 0.5 mg | + | Intramuscularly |
| 14 | 0.5 mg | + | " |
| 28 | 1 mg | + | " |
| 42 | 1 mg | − | Intravenously |
| 56 | 1 mg | − | " |

On day 70 the sheep was exsanguinated.

b. Preparation of [sheep-anti-(rabbit-γ-globulin)] cellulose. The γ-globulin fraction of the sheep serum described under a) was prepared by precipitating it with 16 percent (w/v) solid sodium sulphate. This γ-globulin fraction was bound to m-aminobenzyloxymethyl-cellulose, as described in example Ic).

c. Determination of hyman chorionic gonadotrophin (HCG). A dilution series of HCG was prepared in 0.01 M phosphate buffer of pH 6.0, which also contained 2 percent (v/v) normal sheep serum. The dilution series was in the range of 10 to 320 I.U./l, the dilution factor being 2.

To 5 ml of a HCG solution was added 0.1 ml of a rabbit (anti-HCG) serum (see example Ib), diluted with the same buffer to the desired strength. The mixture was left to stand at room temperature for 30 minutes, after which 1.5 mg. of [sheep-anti(rabbit-γ-globulin)] cellulose were added and the mixture was rotated for 2 hours.

The cellulose was centrifuged for 10 minutes at 3,000 r.p.m. and resuspended in 1 ml of a solution of HCG-HRP coupling product, prepared in accordance with example Ia), diluted to the desired strength with 0.01 M phosphate buffer of pH 6.0 with 2 percent normal sheep serum. The mixture was stirred again for 2 hours. After centrifugation the enzyme activity was determined in the supernatant liquid by adding 0.5 ml of it to 1.5 ml of enzyme substrate consisting of 10 μl of 30 percent $H_2O_2$ and 20 mg of 5-amino-salicylic acid in 150 ml of 0.01 M phosphate buffer of pH 6.0. The mixture was left to stand for 30 minutes at 25°, after which the extinction was measured at 460 nm. In the supernatant liquid 100 percent enzyme activity is measured provided that no anti-HCG serum is added to the system.

A dilution series of HCG, prepared with children's urine as dilution liquid, gave an identical pattern so that also measurings in the urine samples can be performed.

The centrifugation step effects a ten times higher sensitivity than can be reached in a system without centrifugation.

EXAMPLE III

Determination of HCG and LH in low concentrations by means of an enzyme/antibody coupling product.

a. Preparation of the immuno-adsorbent HCG cellulose. This immuno-adsorbent was prepared by the method mentioned in example Ic), but instead of rabbit-γ-globulin, 100 mg of HCG were coupled to 500 mg of m-aminobenzyloxymethyl cellulose.

b. Purification of antibodies against HCG. Ten ml of rattib-anti-HCG serum, prepared in accordance with example Ib), was diluted with 90 ml of 0.05 M citrate of pH 5.0 and slowly led over the immuno-adsorbent, which has packed in a column and mixed with 10 parts of Sephadex G-25. The immuno-adsorbent was washed with the same buffer till no more protein was eluted. The antisubstances were eluted with 0.05 M citrate of pH 2.0. The fractions were collected in one half volume of 0.25 M $NaHCO_3$, tested for their content of antibodies and protein, and the suitable fractions were frozen.

c. Preparation of the coupling product (anti-HCG)-HRP. Twenty mg of horse radish peroxidase (HRP) were dissolved in 2 ml of an antibody solution having a protein content of 2 mg/ml. To this solution were added 8 μl of 25 percent glutaric aldehyde solution, after which the mixture was shaken for 2 hours at room temperature. Finally the mixture was fractionated over a Sephadex G-200 column in 0.05 M phosphate buffer of pH 6.5. The fractions whose highest percentage of enzyme activity were bound to HCG cellulose, were used in the test system.

d. Determination of HCG and LH. Ten ml of a HCG dilution series of HCG and 10 ml of a HCG dilution series of LH were mixed with 5 mg of anti-HCG cellulose, prepared in accordance with example Ic), which was suspended in 1 ml of 0.15 M phosphate buffer of pH 6.0, and the mixtures rotate at room temperature for 2 hours. The immuno-adsorbent was centrifuged and washed with 5 ml of 0.05 M phosphate buffer of pH 6.0.

To the immuno-adsorbent 1 ml of the (anti-HCG)-HRP coupling product was added in the desired dilution, after which the mixture was rrotated again for 2 hours. Finally, after centrifugation, the enzyme activity of the supernatant liquid was determined as described in the previous examples.

By this method a concentration of from 5 to 10 I.U. of HCG and 10 to 20 I.U. of LH per liter respectively could be determined. If the centrifugation step is omitted the optimum sample size is 0.5 nl and the sensitivity about 100 I.U. of HCG per liter, of about 200 I.U. of LH per liter, so that the method according to the invention yields a 10–20 fold increase in sensitivity.

EXAMPLE IV

Determination of HCG and anti-HCG.

a. Rabbit-serum was fractionated over DEAE cellulose in accordance with the prescription of H.A. Sober and others in J. Am. Chem. Soc. 78, 756 (1956). The isolated γ-globulin fraction, which was immuno-electrophoretically pure, was partly used for generating antibodies in a sheep in accordance with the scheme of example IIa), while besides 100 mg of rabbit-γ-globulin was coupled to 500 mg of m-aminobenzyloxymethyl cellulose by the method described in example Ic). From the sheep [anti-(rabbit-γ-γ-globulin)] serum prepared the specific antibodies were isolated by the method described in example IIb) with the immmuno-adsorbent III b. The coupling product [anti-(rabbit-γ-globulin)]-HRP was prepared analogous to the coupling product (anti-HCG)-HRP, described in example IIIc).

c. Determination of anti-HCG. A dilution series of rabbit-(anti-HCG) serum was prepared with 0.05 M phosphate buffer of pH 6.0. Rabbit-(anti-HCG) serum (0.5 ml) was rotated with 0.25 mg of HCG-cellulose for 2 hours (see example IIIa). The reaction mixture was centrifuged and the precipitate washed four times with phosphate buffer, each time with 3 ml, after which the precipitate was resuspended in 1 ml of a solution of the coupling product b. The mixture obtained was again rotated for 2 hours. After centrifugation the enzyme activity in the supernatant liquid was determined, as described in example Id).

d. Determination of HCG. With the reagents prepared, HCG was determined by incubating solutions of it with 0.5 ml of rabbit-(anti-HCG)-serum in a dilution which in the system described under c) just causes an almost maximum reduction in enzyme activity in the supernatant liquid, and performing the process described under c) with the mixture obtained. Where use was made of 5 ml of HCG solution, it proved to be possible to demonstrate concentrations of about 10 I.U./l of HCG.

EXAMPLE V

Determination of insulin in serum.

a. Preparation of insulin-(glucose-oxidase). Five mg of hog insulin and 25 ml of glucose-oxidase were dissolved in 2 ml of 0.05 M phosphate buffer of pH 6.5. To this solution 5 $\gamma$ of 25 percent glutaraldehyde solution was added, after which the mixture was shaken at room temperature for 90 minutes. The mixture was fractionated over Sephadex G-200 in 0.05 M phosphate buffer of pH 6.5. The fractions whose highest percentage of enzyme activity could be bound by antibodies against insulin were used in the test system.

b. Preparation of antibodies against insulin. Ten caviae were injected intramuscularly, once a week, with 1 mg of hog insulin in complete Freund's adjuvant, over a period of from 4 to 8 weeks. After having been left alone for 2 weeks the animals were injected intravenously with another milligram of insulin without adjuvant. Another 2 weeks later the animals were exsanguinated. Hypoglycemia occurring occasionally was combated by intraperitoneal administration of glucose.

c. Preparation of anti-substances against cavia $\gamma$-globulin. Cavia $\gamma$-globulin was prepared by adding one volume of saturated ammonium sulphate solution to two volumes of cavia serum. The resulting precipitate was washed twice with 33 percent saturated $(NH_4)_2SO_4$ solution and then taken up in a physiological salt solution. A sheep was immunized with increasing dosages of the $\gamma$-globulin prepared, viz. 0, 5, 1 and 2 mg. The injections were given every 2 weeks, the immunogen being mixed with complete Freund's adjuvant. Two weeks after the last injection another 2 mg of $\gamma$-globulin, in a physiological salt solution, were given. One week later the animal was exsanguinated.

d. Preparation of insoluble antibodies against cavia $\gamma$-globulin. Ten gm of microcrystalline cellulose were activated by adding it, while stirring, to 400 ml of 2.5 percent (w/v) CNBr-solution, after which the pH was adjusted to 10.5 with an 1 N NaOH-solution, and it was maintained at it for 2 minutes. The cellulose was washed with ice water and with 0.1 M $NaHCO_3$. To 10 ml of sheep-anti-(cavia $\gamma$-globulin) serum 1.6 gm of $NaSO_4$ were added. After stirring for 1 hour at room temperature the precipitate was centrifuged, washed twice with 20 ml of 16 percent (w/v) $Na_2SO_4$ solution, and finally taken up in 10 ml of 0.1 M $NaHCO_3$.

The activated cellulose was mixed with 40 ml of a 0.1 M $NaHCO_3$ solution and the 10 ml of $\gamma$-globulin solution. This suspension was rotated for 40 hours at 4° C and washed, twice with 5 ml of 0.5 M $NaHCO_3$, twice with 500 ml of 0.05 M citrate of pH 1.1, and two times with 500 ml of 0.05 M phosphate of pH 6.2.

e. Determination of insulin in serum. Four ml of an insulin dilution series in the range of from 0–100 ng/ml, were incubated at room temperature, for 4 hours, with 1.0 ml of anti-insulin serum (with 0.15 M phosphate buffer of pH 6.0, diluted to the desired strength). After that 5 mg of the immuno-adsorbent prepared under d), suspended in 1 ml of 0.15 M phosphate buffer of pH 6.0, were added, and the resulting mixture rotated overnight at 4° C. Then the immuno-adsorbent was centrifuged and washed three times with 5 ml of 0.05 M phosphate buffer of pH 6.0 (each time with 5 ml), to which 2 percent sheep serum had been added. After that 1.0 ml of insulin-glucose oxidase, diluted to the desired strength with the wash buffer, was added to the immuno-adsorbent. The mixture obtained was again rotated overnight and centrifuged, after which the enzyme activity in the supernatant liquid was measured by incubating 0.5 ml of it with 2.5 ml of a substrate solution, and the extinction measured at 460 nm. The substrate solution contained 50 mg of glucose, 10 $\mu$gm of peroxidase and 1 mg of 5-aminosalicylic acid per 2.5 ml of 0.05 M phosphate buffer of pH 6.0.

The centrifugation step, in this case serving both to raise the maximum volume of the test liquid to be employed and to remove serum factors disturbing the reaction, caused a 10-fold increase in sensitivity, so that a concentration of a few ng/ml of insulin could be demonstrated.

EXAMPLE VI

Determination of oestradiol.

a. Preparation of oestradiol-17-succinyl-HRP. Fifty mg of oestradiol-17-haemisuccinate and 0.08 ml of tri-n-butylamine were dissolved in 2.5 ml of dioxane. To the cold solution (2° C) 15 $\mu$l of isobutylchlorocarbonate were added. After 30 minutes this solution was mixed with 100 mg of horse radish peroxidase (HRP) in 7.5 ml of mixture of dioxane and water (2:3), which had been adjusted to pH 9.5 with caustic soda. This solution was stirred for 4 hours at 2° C, after which it was dialysed for 18 hours. The precipitate obtained after the pH of the dialysate had been adjusted to 4.6 was centrifuged, washed, and taken up in 5 ml of distilled water, which had been adjusted to pH 8. The material was purified further by precipitating it twice with 10 ml of acetone. The ultimate product was taken up in 10 ml of 0.05 M phosphate buffer of pH 7.8.

b. Preparation of oestradiol-17-succinyl-BSA. The preparation was prepared by the mixed anhydride method as described under a). The starting material was 100 mg of oestradiol-17-haemisuccinate and 150 mg of bovine serum albumin (BSA).

c. Preparation of anti-substances against oestradiol. A sheep was injected every 4 weeks with 4 mg of oestradiol-17-succinyl-BSA in complete Freund's adjuvant. With regular intervals blood was taken from the sheep. The serum was adsorbed with BSA.

Preparation of anti-substances against sheep $\gamma$-globulin. Sheep-$\gamma$-globulin was prepared as described in example IIb), this time, however, with 16 percent w/v sodium sulphate. Rabbits were immunized with this sheep-γ-globulin in accordance with the following scheme:

| Day | Quantity | Freund's adjuvant | Manner of injection |
|---|---|---|---|
| 0 | 200 μgm | + | Intramuscularly |
| 14 | 400 μgm | + | " |
| 28 | 800 μgm | + | " |
| 42 | 800 μgm | − | Intravenously |

Two weeks after the last injection the animals were exsanguinated.

e. Preparation of the immuno-adsorbent [rabbit-anti(-sheep-γ-globulin)] cellulose.

The γ-globulin fraction of the anti-sera described under b) was prepared by precipitation with 18 percent w/v $Na_2SO_4$. The product obtained was coupled with cellulose by Gurvich's method described in example Ic).

f. Determination of oestradiol. A dilution series of oestradiol (0–0.5–1–2–4–8–16 ng/ml) was prepared in phosphate buffer of pH 6.0. Five ml of sample were mixed with 0.5 ml of the sheep-antioestradiol-serum in the desired dilution. After incubating the mixture for 2 hours at room temperature 1 ml of immuno-adsorbent suspension (see e) of 60 mg/ml was added, after which the mixture was rotated for 4 hours at room temperature. The cellulose was centrifuged and washed with 5 ml of 0.05 M phosphate buffer of pH 6.0 containing 2 percent BSA. Then 1 ml of oestradiol-17-succinyl-HRP, diluted to the desired strength with the buffer with which the mixture was washed, was added to the cellulose. The mixture was rotated for 1 hour, after which it was centrifuged again and the enzyme activity in the supernatant liquid was measured as described in example I. By the method described concentrations of 1 ng/ml of oestradiol could be demonstrated, which means an increase in sensitivity by a factor 10, coompared with the test without centrifugation step.

EXAMPLE VII

Determination of cortisol.

a. Preparation of cortisol-21-galactose-oxidase.

Fifty mg of cortisol-21-haemisuccinate and 100 mg of galactose-oxidase were coupled by the mixed anhydride method as described in example VIa).

b. Preparation of insoluble transcortine. One hundred mg of transcortine purified by DEAE cellulose chromatography, followed by hydroxylapatite chromatography, were coupled with 3 gm of Sepharose 4B by the CNBr method: Sepharose 4B suspension (3 gm) was activated by mixing it with 4 ml of 2.5 percent (w/v) CNBr-solution in distilled water, after which the pH was adjusted to 1 N NaOH between 10 and 11, at which value it was maintained for 6 minutes. Then the Sepharose was washed with ice-water and with 0.1 M $NaHCO_3$, after which 100 mg of transcortine in 20 ml og 0.1 M $NaHCO_3$ were added, and the suspension was shaken at 4° C for 24 hours. After being washed successively with 0.5 M $NaHCO_3$, 0.05 M citrate buffer of pH 1.1 and 0.05 M phosphate buffer of pH 6.0, the Sepharose was kept in the last buffer, to which 0.1 percent merthiolate had been added.

c. Determination of cortisol. A cortisol dilution series, in the range of from 0.25–16 ng/ml was prepared in 0.05 M phosphate buffer of pH 6.0. File ml of each cortisol solution (in 0.5 M phosphate buffer of pH 6.0) were rotated overnight with 5 mg of transcortine-Sepharose, at 4° C. After centrifugation 1 ml of cortisol-21-galactose oxidase solution, diluted to a suitable concentration in the buffer mentioned before, was added, after which the mixture was rotated for 2 hours at 4° C. After recentrifugation the enzyme activity in the supernatant liquid was determined by adding 0.5 ml of it to 1.5 ml of substrate consisting of 100 mg of D-galactose, 20 mg of 5-amino-salicylic acid and 10 μgm of peroxidase in 150 ml of 0.02 M phosphate buffer of pH 6.0. Finally, after 30 minutes, the extinction was measured at 460 nm.

By this method about 1 ng/ml cortisol could be demonstrated, which means an increase in sensitivity by a factor 10.

We claim:

1. Process for the demonstration and determination of a component of the reaction between a bindable substance selected from the group consisting of an antigen, a hapten, and a low molecular substance, and a protein capable of binding said bindable substance specifically, said protein being selected from the group consisting of an antibody and a specific binding protein, comprising the steps of:

a. providing a given quantity of the binding partner of the component to be determined, which binding partner is in an insoluble form;

b. reacting the component to be determined with its binding partner to form a reaction mixture having a solid phase and a liquid phase;

c. separating the solid phase from the liquid phase;

d. adding to said solid phase a given quantity of a coupling product of the component to be determined with an enzyme; and e. determining the enzyme activity of the solid phase which is a measure of the quantity of reaction component to be determined.

2. Process for the demonstration and determination of a component of the reaction between a bindable substance selected from the group consisting of an antigen, a hapten and a low molecular substance, and a protein capable of binding said bindable substance specifically, said protein being selected from the group consisting of an antibody and a specific binding protein, comprising the steps of:

a. providing a given quantity of the binding partner of the component to be determined in a soluble form;

*b. reacting the component to be determined with its binding partner;*

[b.] *c.* adding a given quantity of an antibody against said binding partner, which antibody is in an insoluble form, to form a reaction mixture having a solid phase and a liquid phase;

[c.] *d.* separating the solid phase from the liquid phase;

[d.] *e.* adding to said solid phase a given quantity of a coupling product of the component to be determined with an enzyme; and

[e.] *f.* determining the enzyme activity of either the liquid phase of the solid phase, which activity is a measure of the quantity of the reaction component to be determined.

3. The process of claim 1 in which the enzyme is an oxido-reductase.

4. The process of claim 2 in which the enzyme is an oxido-reductase.

*5. Process for the demonstration and determination of a component of the reaction between a bindable substance selected from the group consisting of an antigen, a hapten, and a low molecular substance, and a protein capable of binding said bindable substance specifically, said protein being selected from the group consisting of an antibody and a specific binding protein, comprising the steps of:*

*a. providing a given quantity of the binding partner of the component to be determined, which binding partner is in an insoluble form;*

*b. reacting the component to be determined with its binding partner to form a reaction mixture having a solid phase and a liquid phase;*

*c. separating the solid phase from the liquid phase;*

*d. adding to said solid phase a given quantity of a coupling product obtained by binding a substance capable of reacting specifically with one of the reaction components, to an enzyme; and*

*e. determining the enzyme activity of the solid phase which is a measure of the quantity of reaction component to be determined.*

*6. Process for the demonstration and determination of a component of the reaction between a bindable substance selected from the group consisting of an antigen, a hapten, and a low molecular substance, and a protein capable of binding said bindable substance specifically, said protein being selected from the group consisting of an antibody and a specific binding protein, comprising the steps of:*

*a. providing a given quantity of the binding partner of the component to be determined in a soluble form;*

*b. reacting the component to be determined with its binding partner;*

*c. adding a given quantity of antibody against said binding partner, which antibody is in an insoluble form, to form a reaction mixture having a solid phase and a liquid phase;*

*d. separating the solid phase from the liquid phase;*

*e. adding to said solid phase a given quantity of a coupling product obtained by binding a substance capable of reacting specifically with one of the reaction components, to an enzyme; and*

*f. determining the enzyme activity of either the liquid phase or the solid phase, which activity is a measure of the quantity of the reaction component to be determined.*

* * * * *